United States Patent [19]

Townsend et al.

[11] Patent Number: 4,935,505

[45] Date of Patent: Jun. 19, 1990

[54] AZOLO [1,3] DIAZEPINE-5-OL COMPOUNDS AND THEIR USES

[76] Inventors: Leroy B. Townsend, 1400 Folkstone Ct.; Oscar L. Acevedo, 1325 McIntyre, both of Ann Arbor, Mich. 48105

[21] Appl. No.: 154,510

[22] Filed: Feb. 4, 1988

Related U.S. Application Data

[63] Continuation of Ser. No. 491,177, May 3, 1983, abandoned.

[51] Int. Cl.$^5$ ................. C07H 19/167; C07H 19/173; C07H 17/02; A61K 31/70
[52] U.S. Cl. ..................................................... 536/24
[58] Field of Search ............................ 536/24; 514/43

[56] References Cited

U.S. PATENT DOCUMENTS

| | | | |
|---|---|---|---|
| 3,598,807 | 8/1971 | Nakayama et al. | 536/24 |
| 3,923,785 | 12/1975 | Ryder et al. | 536/24 |
| 3,959,257 | 5/1976 | Umezawa et al. | 536/24 |
| 4,195,176 | 3/1980 | Baker et al. | 536/24 |
| 4,299,823 | 11/1981 | Rideout et al. | 514/49 |

OTHER PUBLICATIONS

Elliott et al., Analogs of 8-azaguanosine, Chem Abstracts 85:116642v (1976).
Kanamitsu, Microbial Preduction of Ribosides of Pyrazolo(3,4-d)-Pyrimidines, Chem. Abstracts 80:94260m (1973).
Lichtenthaler et al., Nucleosides 38, The Ribonucleosides of Allopurinol, Chem. Abstracts 95:62573j (1981).
Fryer et al., Quinazolines and 1,4-Benzodiazepines, LXXXVI, The Synthesis of . . . Imidazopyrazolodiazepines, Chem. Abstracts 90:63716 (1978).

Primary Examiner—Johnnie R. Brown
Assistant Examiner—Gary L. Kunz

[57] ABSTRACT

Novel azolo [1,3] diazepine compounds of the formula:

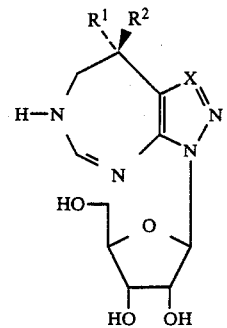

wherein $R^1$ and $R^2$ are either H or OH and $R^1$ and $R^2$ are not the same and X is either CH or N. Such compounds are active as adenosine deaminase inhibitors.

3 Claims, 1 Drawing Sheet

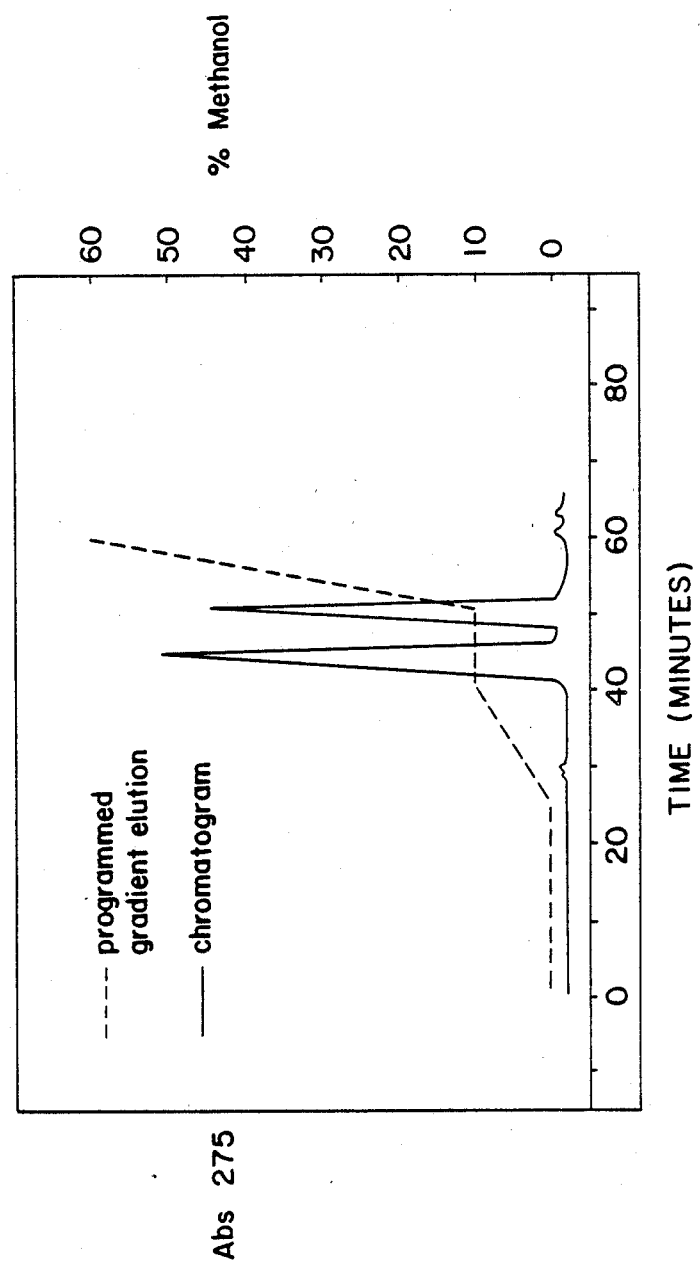

AZOLO [1,3] DIAZEPINE-5-OL COMPOUNDS AND THEIR USES

This is a continuation of co-pending application Ser. No. 491,177 filed on May 3, 1983, now abandoned.

This invention was produced with the support of the National Cancer Institute, National Institute of Health, United States Government and the UNDP/World Bank/WHO Special Program for research and training in typical disease and the Scientific Working group on Filariasis.

BACKGROUND OF THE INVENTION

1. Field of the Invention

This invention relates to new chemical compounds and more particularly to novel bicyclic azolo[1,3]diazepine derivatives.

2. Description of the Prior Art

In a recent publication by Chan et al, J. Org. Chem., 1982, 47, 3457, the synthesis of the potent adenosine deaminase inhibitor pentostatin, (i.e., 8(R)-3-(2-deoxy-β-D-erythro-pentofuranosyl)-3,6,7,8-tetrahydroimidazo[4,6-d][1,3]diazepin-8-ol) with the following structure, compound 1,

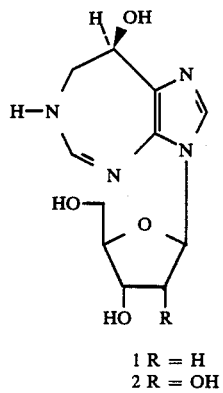

1 R = H
2 R = OH and structurally related to the natural product coformycin, compound 2, was disclosed. Thus, it is now known that pentostatin, 1, like coformycin, 2, are exceedingly tight binding inhibitors of human erythrocytic adenosine deaminase, exhibiting $Ki=1\times10^{-12}M$ and $Ki=1\times10^{-11}M$, respectively. In combination with 9-β-D-arabinofuranosyl adenine, pentostatin has shown dramatic antitumor effects both in vitro and in vivo. However, the acute renal toxicity of pentostatin in clinical trials (see, Mitchell et al, R. Blood, 1980, 56, 556 and Cancer Treat. Rep., 1979, 63, 1439) has initiated a search for other (see Baker et al, J. Org. Chem., 1982, 47, 2179) strong inhibitors of the enzyme which might lack these unfortunate side effects.

SUMMARY OF THE INVENTION

The present invention is directed to new compounds and particularly to N-substituted azolo[1,3]diazepine derivatives wherein the N-substituent is selected from the group comprising methyl, β-D-ribofuranosyl [this group could also include other alkyl substituents, aryl substituents and carbohydrate substituents, including 2-deoxy-β-D-ribofuranosyl]; the azolo ring system from the group comprising pyrazole, v triazole [this group could also include imidazole, pyrrole, s-triazole, and mixed heterocyclic azoles]; and the 1,3-diazepine-5-ol ring system.

The instant invention is further directed to and provides a total synthesis of some heterocyclic analogs of coformycin, 2, the 2-hydroxy analog of pentostatin, 1. Thus, the invention provides a facile reaction sequence leading to the synthesis of nucleosides containing the 3,4,5-trihydro-1,3-diazepin-5-ol moiety and in particular the following compound 3 and 4, sharing in common with compound 1 and 2 an aglycon with the 3,4,5-trihydro-1,3-diazepin-5(R)-ol moiety fused to a unique 5-membered heterocyclic ring as follows:

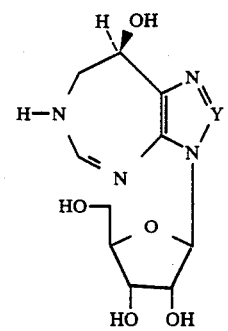

3 X = CH, Y = N
4 X = Y = N

BRIEF DESCRIPTION OF THE DRAWING

The FIGURE illustrates the HPCL chromatographic separation of a mixture of R and S isomers of 6,7,8-trihydro-3-β-D-ribofuranosyl-v-triazolo[4,5-d][1,3]diazepin-8-ol synthesized according to the present invention.

DESCRIPTION OF THE PREFERRED EMBODIMENTS

In order to more fully describe the method of synthesizing the novel azolo [1,3] diazepine-5-ol compounds according to the present invention and the basis upon which the methodology was developed, the following series of reaction schemes are presented illustrating the preferred embodiments. In presenting the following reaction schemes, the reactants, intermediates and products are designated by the underlined numbers.

Reaction Scheme I exemplifies the synthesis of a model compound as follows:

SCHEME I

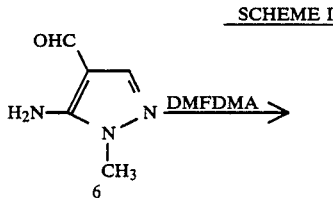

6

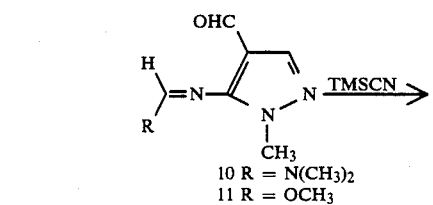

10 R = N(CH₃)₂
11 R = OCH₃

-continued
SCHEME I

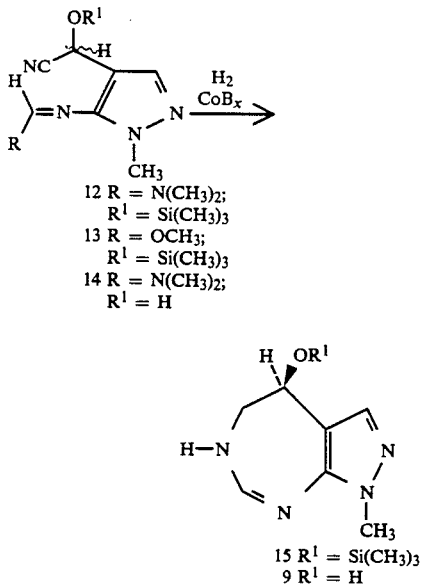

12 R = N(CH₃)₂;
   R¹ = Si(CH₃)₃
13 R = OCH₃;
   R¹ = Si(CH₃)₃
14 R = N(CH₃)₂;
   R¹ = H

15 R¹ = Si(CH₃)₃
9 R¹ = H

The objective was to build the 3,4,5-trihydro-1,3-diazepin-5-ol moiety using as a template the 5-amino-1-methylpyrazole-4-carboxaldehyde, 6. This aldehyde may be readily prepared from the partial reduction and in situ hydrolysis of the corresponding nitrile, compound 5.

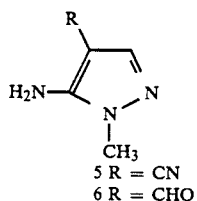

5 R = CN
6 R = CHO

The presentation of the aldehyde 6 involved the reduction of nitrile 5 with an activated form of Raney nickel (see Dominquez et al, J. Org. Chem. 1961, 26, 1625; T-1 Raney Nickel) in 70% aqueous acetic acid. Through a modification of the Kiliani-Fischer cyanohydrin homologation sequence, it was proposed to add hydrogen cyanide in this aldehyde and subsequently to reduce the nitrile portion of the resulting cyanohydrin 7.

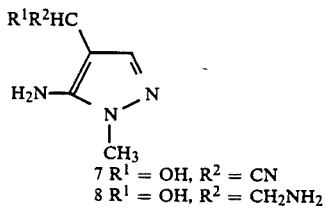

7 R¹ = OH, R² = CN
8 R¹ = OH, R² = CH₂NH₂

This transformation would provide the 5-amino-4-(β-amino-α-hydroxyethyl)-1-methylpyrazole, intermediate 8. This intermediate would be subsequently ring closed with triethylorthoformate to afford the requisite 4,5,6-trihydro-1-methylpyrazolo[5,4-d] [1,2] diazepin-4-ol, compound 9.

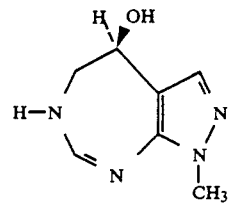

9

In practice, the reaction of the aldehyde 6 with hydrogen cyanide-potassium cyanide in methylene chloride did not given an appreciable yield of the cyanohydrin at room temperature. Under forcing conditions (HCN/KCN; CH₂Cl₂; 75°; stainless steel reaction vessel), large amounts of dimeric material were isolated as the predominant product. Thus, it was concluded that prior protection of the amine functionality of compound 6 was necessary in order to effect a nucleophilic reaction of cyanide ion at the electron rich aldehyde carbonyl carbon.

A protection of the amine functionality of aldehyde 6, using dimethylformamide dimethylacetal, gave the crystalline formylated product 10. This protecting group was stable to all reaction conditions, save those employing strong base. Formulation of all ortho-amino aldehydes gave excellent yields of the corresponding N,N-dimethylamino-formylated products as in compound 10. However, there was contained in each product a small impurity of the methoxy-formylated product, as in compound 11. When these compounds were separated on silica gel, compounds 10 and 11 were shown to give different and distinct trimethylsilyl cyanohydrins 12 and 13, respectively. The trimethylsilyl cyanohydrins 12 and 13 were in turn hydrogenated to afford an identical mixture of 15 and 9 in each case.

The treatment of the formylated aldehyde, compound 10, with trimethylsilyl cyanide in the presence of dry, powdered zinc chloride, under an atmosphere of nitrogen provided an excellent yield of the trimethylsilyl cyanohydrin, 12. The 5-(N,N-dimethylamino methyleneamino)-4-(cyano[trimethylsiloxy]methyl)-1-methylpyrazole, 12, was remarkably stable and may be purified by trituration under anhydrous hexane or by silica gel chromatography, using anhydrous techniques as described later.

Extensive experimentation with different methods of chemical and catalytic reduction of the nitrile group of compound 12 revealed that a catalytic hydrogenation of this group was the superior method. In particular, the use of lithium aluminum hydride, or sodium borohydride-trifluoroacetic acid complex, or the lithium aluminum hydride-trialkoxide reagents gave in each case no descernible 1,3-diazepine products. Only large amounts of dimeric materials and starting material were isolated. It was found that the cobalt or nickel boride catalysts (see U.S. Pat. No. 3,322,686) under 30–35 atm of hydrogen effected the desired reduction and an in situ annulation, with a concomitant loss of dimethylamine. The reduction gave as products the 1,3-diazepines 15 and 9. The trimethylsilyl ether 15 was readily converted to the alcohol 9 in an acidic hydrolysis of the trimethylsilyl group.

That the 3,4,5-trihydro-1,3-diazepin-4-ol moiety had been created in this transformation was confirmed by the ¹H NMR spectrum of the product, compound 9.

The spectrum revealed a coupling between the vinylogous H(7) proton and the adjacent N(6) proton; resonances for the methylene protons [H(7) and H(7b)], and the balance of a resonance peak for the dimethylamine protons (see Table I).

TABLE I
$^1$H NMR (360 MHZ) Chemical Shifts Of 1,3-Diazepin-5-ol Moieties

| Compound[a] | Vinylic | —CH$_2$— | Methine | N—H[b] |
|---|---|---|---|---|
| 9 | 6.86 | 3.22–3.02 (m) | 4.58 (m) | 7.6 (m) |
| 25[c] | 6.58(d), 6.42(d) | 3.43–3.26 (m) | 4.09 (m) | 6.1 (m) |
| 36 | 7.18 (d) | 3.31–3.21 (m) | 4.05 (m) | 8.3 (m) |

[a] spectra taken in DMSO-$d_6$ with tetramethylsilane as internal standard.
d = doublet, m = multiplet.
[b] Exchanges with deuterium oxide.
[c] Spectrum taken in CDCl$_3$ with tetramethylsilane as internal standard.

Reaction Scheme II represents an extension of the methodology described in Scheme I by the synthesis of the 4(R,S)-4,5,6-trihydro-1-($\beta$-D-ribofuransoyl)-pryazolo[5,4-d][1,3]diiazepin-4-ol. This synthesis of the 1-$\beta$-D-ribofuranosyl analog of compound 9 was accomplished in the following manner.

SCHEME II

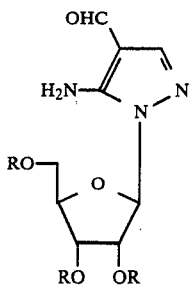

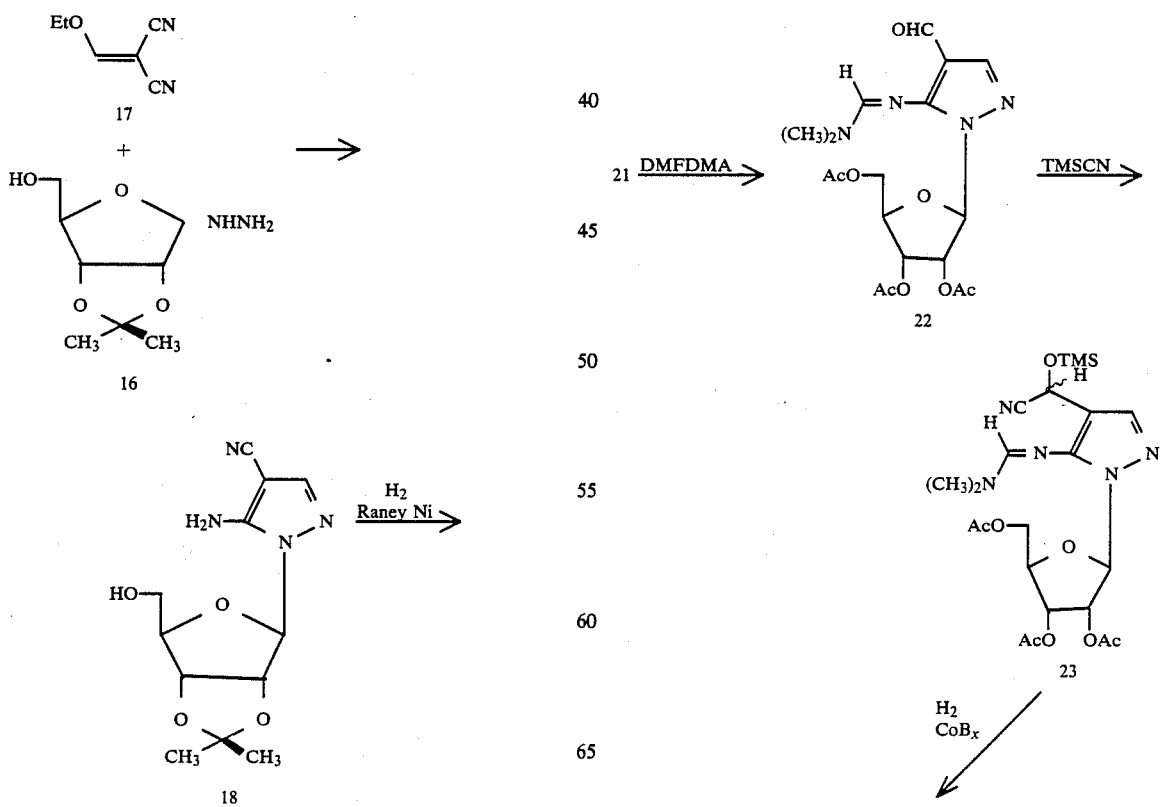

SCHEME II
-continued

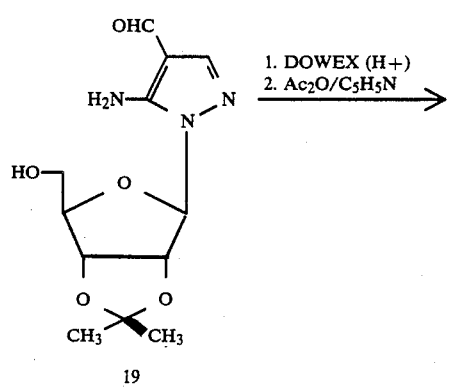

-continued
SCHEME II

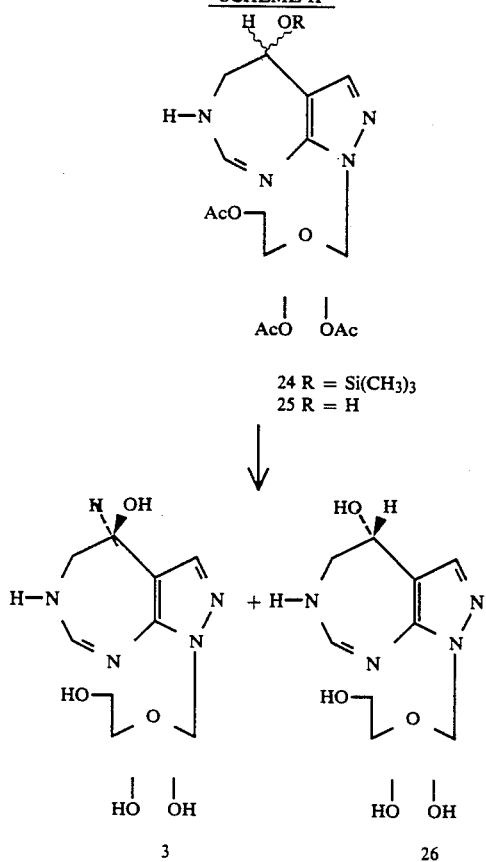

24 R = Si(CH₃)₃
25 R = H

Acetonation of D-ribose, followed by a condensation of the 2,3-O-isopropylidene-D-ribose with anhydrous hydrazine provided an excellent yield of the 1-deoxy-1-hydrazinyl-2,3-O-isopropyliden-D-ribose, compound 16. A subsequent condensation of 16 with ethoxymethylene malononitrile, 17, in ethanol, gave a single nucleoside product. This nucleoside was characterized as the 5-amino-4-cyano-1-(2,3-O-isopropylidene-β-D-ribofuranosyl)pyrazole, 18, on the basis of its ultraviolet and ¹H NMR Spectra as well as its elemental analysis (C, H, N). The ortho-amino nitrile 18 was reduced catalytically in a buffered solution consisting of pyridne-glacial acetic acid-water to afford a moderate yield of the ortho-amino aldehyde 19.

In anticipation of the projected instability (see Ohne et al, J. Am. Chem. Soc. 1974, 96, 4326) to acid of the target compound 3, the next step was to exchange the acid labile isopropylidene protecting group of the ribofuranosyl moiety of 19 for the base labile acetyl protecting groups of compound 21. The isopropylidene group was removed from compound 19 by a treatment with DOWEX 1×4 (H+) ion-exchange resin in methanol. The aldehyde 20, which precipitated during the course of deprotection, was filtered (along with the spent resin), dried over phosphorous pentoxide, and immediately treated with pyridine and acetic anhydride. This procedure furnished the crystalline 5-amino-1-(2,3,5-tri-O-acetyl-β-D-ribofuranosyl) pyrazole-4-carboxaldehyde, 21, in 61% overall yield.

As in the case of the model compound 6, the aldehyde was smoothly formylated using a five-fold excess of dimethylformamide dimethylacetal in anhydrous methylene chloride to yield aldehyde 22. Compound 22 was reacted with neat trimethylsilyl cyanide, using boron trifluoride-etherate in ether as a Lewis acid catalyst. The diastereomeric trimethylsilyl cyanohydrins 23 were isolated using anhydrous low-pressure chromatography techniques as described later. A reduction of the nitrile functionalities of 23, using a cobalt boride catalyst and 30 atm of hydrogen and an in situ annulation proceeded in an overall yield of 45%. The product was isolated as a mixture of the trimethylsilyl ether 24 and the alcohol 25; however, pure 25 was obtained from an acidic hydrolysis of the trimethylsilyl group of 24 in the mixture. The ¹H NMR (360 MHz) spectrum of the R and S mixture at C(4) represented by structure 25 revealed the presence of two very similar compounds in a ratio of 2:1. This proportionality was determined by an integration of the signals for the H(7), H(3), and H(1') protons, each of which were cleanly resolved for each diastereomer in the mixture (see Table I).

A gentle removal of the acetyl protecting groups of the -D-ribofuranosyl moiety of 25 was effected by treatment of the mixture with methanolic sodium methoxide. The product of this deprotection, which consisted of a mixture of compounds 3 and 26, was precipitated from absolute ethanol to furnish a material which was supportive in its ultra-violet, ¹H NMR, and ¹³C NMR (See Table II) spectra and in its elemental analysis for the 4(R,S)-4,5,6-trihydro-1-(β-D-ribofuranosyl)-pyrazolo[5,4-d][1,3] diazepin-4-ol. In particular, the ¹H NMR (360 MHZ) spectrum of this mixture exhibited a single signal for each type of proton of both compounds, attesting to their similarity. The HPLC techniques did not resolve this mixture.

TABLE II

¹³C—NMR Data for the Diastereomeric Mixture of 4,5,6-Trihydro-1-[β-D-ribofuranosyl)pyrazolo[5,4-d] [1,3]diazepin-4(R,S)-ol Nucleosides 3 and 26.

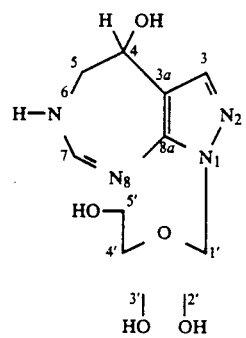

| Carbon | Major Isomer[a] | Minor Isomer |
|---|---|---|
| C(3) | 137.41 | 137.41 |
| C(4) | 63.46 | 63.49 |
| C(5) | 49.84 | 49.84 |
| C(7) | 147.66 | 147.61 |
| C(3a) | 113.29 | 113.34 |
| C(8a)[b] | 144.66 | 144.52 |
| C(1')[c] | 87.69 | 87.64 |
| C(2') | 73.70 | 73.70 |
| C(3') | 70.94 | 70.98 |
| C(4') | 84.49 | 84.49 |

TABLE II-continued $^{13}$C—NMR Data for the Diastereomeric Mixture of 4,5,6-Trihydro-1-[β-D-ribofuranosyl)pyrazolo[5,4-d] [1,3]diazepin-4(R,S)-ol Nucleosides 3 and 26.

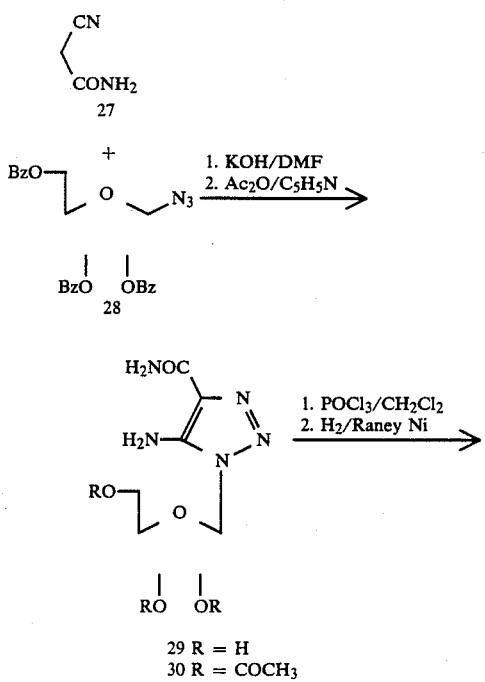

| Carbon | Major Isomer[a] | Minor Isomer |
|---|---|---|
| C(5') | 62.57 | 62.57 |

[a]Chemical shifts are expressed in ppm values downfield from Me$_4$Si. Values were measured relative to an internal DMSO standard and converted to the Me$_4$Si scale using (Me$_4$Si) = (DMSO)−39.50 ppm. Concentration: 15 mg/0.3 mL DMSO-d$_6$. Temp. ca. 27°.

[b]Unambiguous assignment of the bridgehead signals was made from a three-bond $^{13}$C—H decoupling of the H(1') proton with the C(8a) carbon and a similar decoupling of the H(7) proton with the C(8a) carbon. For details of this decoupling technique see Cline et al, J. Chem. Soc., Perkin Trans. II, 1980, 1586 and Opella et al, J. Chem. Phys., 1976, 64,2533.

[c]The chemical shift sequence for the carbons of the β-D-ribofuranosyl moiety havebeen well established for similarly substituted nucleosides.

Reaction Scheme III represents the synthesis of the 8 (R,S)-6,7,8-trihydro-3-β-D-ribofuranosyl-v-triazolo [4,5-d][1,3] diazepin-8-ol as follows:

SCHEME III

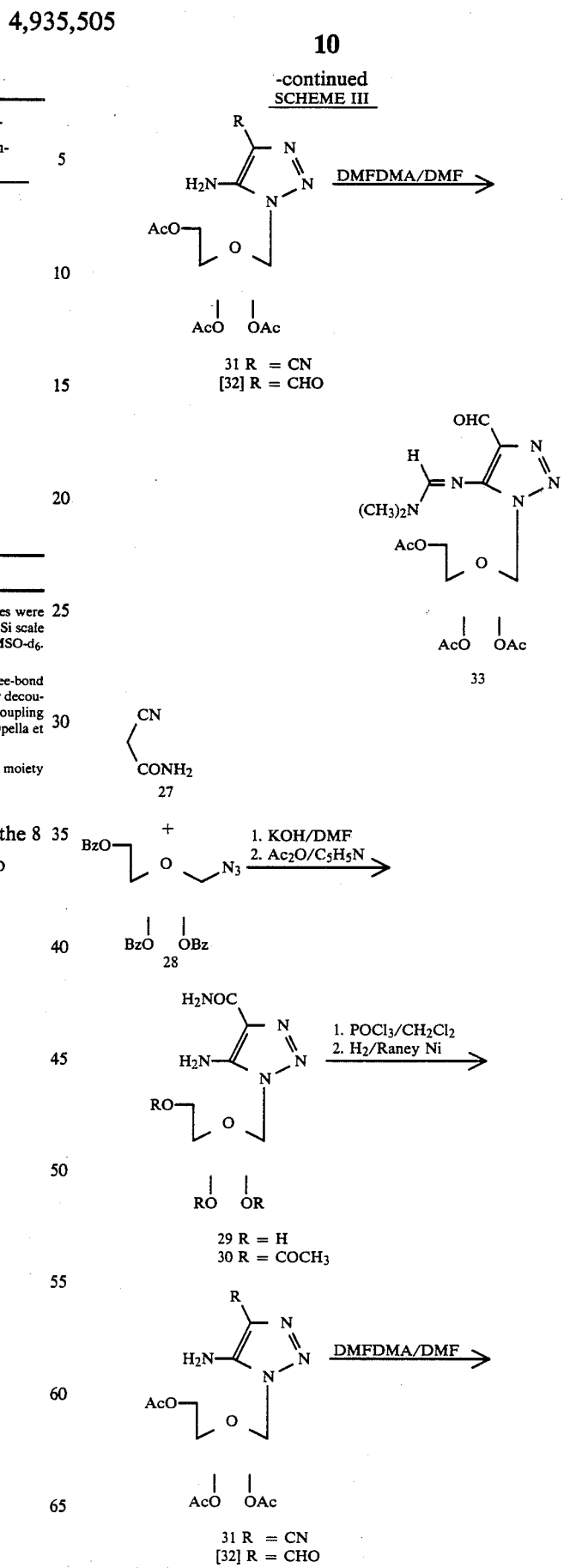

-continued
SCHEME III

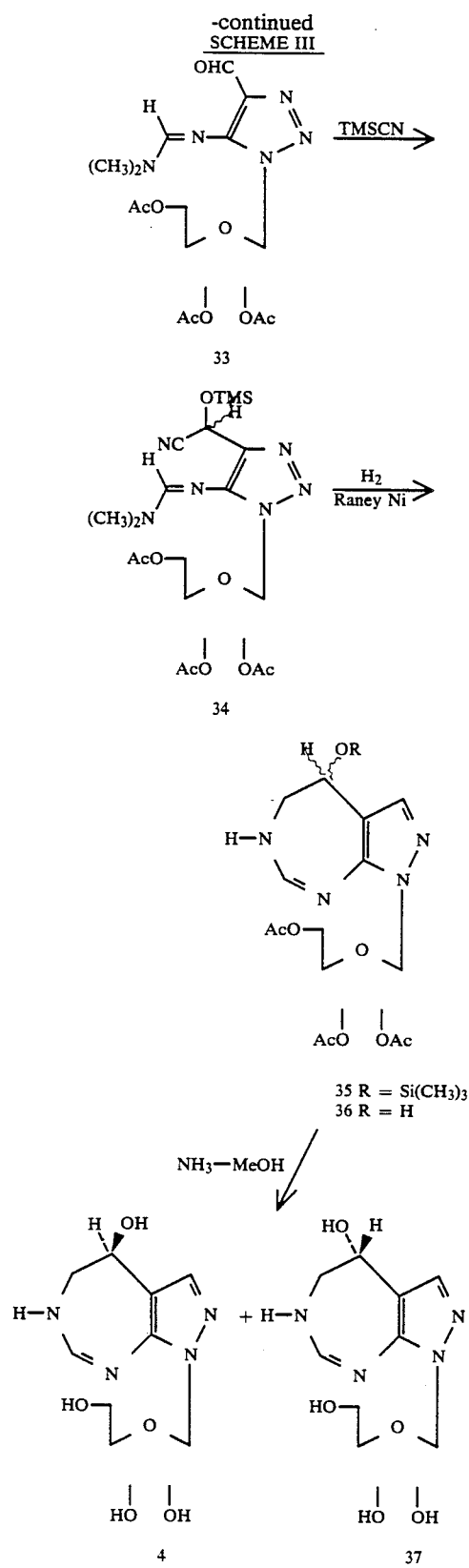

35 R = Si(CH$_3$)$_3$
36 R = H

As illustrated, the synthesis of the 3,4,5-trihydro-1,3-diazepin-5-ol moiety used a v-triazole nucleoside as the starting material. The synthesis of the target compounds, namely the 8(R,S)-6,7,8-trihydro-3-β-D-ribofuranosyl-v-triazolo [4,5,-d][1,3] diazepin-8-ol, 4 and 37, using the methodology described in Schemes I and II, confirmed that this synthetic route is a general method for the synthesis of the 3,4,5-trihydro-1,3-diazepin-5-ol moiety using a variety of hereocycles as the parent rings. Furthermore, the target molecule would allow for the determination of the relative importance of the N(1) nitrogen of coformycin 2 as a binding site for the enzyme adeosine deaminase.

The starting material for this synthesis was the 5-amino-1-(2,3,5-tri-O-acetyl-β-D-ribofuranosyl)-v-triazole, compound 30. A moderate yield of this nucleoside was isolated on a preparative scale, through a modification of an established literature procedure (see Hutzenlaub et al, J. Med. Chem. 1972, 15, 879). This modification produced the triacetate 30 from the 1,3-dipolar cycloaddition of cyanoacetamide and the 1-deoxy-2,3,5-tri-O-benzoyl-β-D-ribofuranosyl azide under strongly basic conditions. A complete removal of the benzoyl protecting groups from the crude nucleoside product (partial removal of these groups had occurred during the course of the reaction) was effected by the use of methanolic sodium methoxide. The procedure was followed by an in situ acetylation of 29 as a crude product, thus producing compound 30 in 37% overall yield.

The dehydration of the carboxamide group 30, using P-toluenesulfonyl chloride in pyridine, provided the corresponding nitrile, compound 31, in fair yield. The actual yield, however, was greatly diminished due to the efforts in isolating this compound in an acceptable purity. Regardless of the efforts to purify this compound, the nitrile 31 was never completely rid of p-toluenesulfonic acid as a contaminant. Best yields (68%) of compound 31 were obtained from the rapid addition of excess phosphorous oxychloride at room temperature to a suspension of the carboxamide 30 in chloroform and triethyl amine. A rapid aqueous workup of this reaction, followed by flash chromatography on silica gel provided the nitrile as a thick syrup.

The nitrile 31 was rapidly reduced to the aldehyde 32 using Raney nickel and 1 atm of hydrogen. Using a buffered solution of pyridine-glacial acetic acid-water, a millimolar solution of the nitrile was reduced in less than 1 hour. The yield of aldehyde 32 from this reduction is directly dependent upon the speed with which the solvents used in reduction are evaporated and the product purified by flash chromatography. Alternatively, after a thorough evaporation of the buffered solvents, the crude product obtained could be immediately treated with dimethylformamide dimethylacetal. This procedure avoided the prolonged handling of the unstable aldehyde and provided a moderate (45%) yield of the formylated aldehyde 33. The chemical stability of the N,N-dimethylamino formyl group allowed for the use of normal chromatographic techniques to obtain analytically pure samples of compound 33.

The formylated aldehyde added trimethylsilyl cyanide smoothly under the catalysis of boron trifluoride-etherate (in ether) at room temperature. Despite the precautions taken to maintain anhydrous conditions during the preparation and isolation of cyanohydrins 34, low-pressure chromatography yielded these compounds in a disappointingly low 45% yield. With continued elution of the low-pressure column used to isolate this mixture, 20–25% yields of the starting material aldehyde 34 were isolated from the almost unavoidable hydrolysis of cyanohydrins. The diastereomeric cyanohydrins were characterized in part by a $^1$H NMR Spectrum which contained resonance peaks for the trimethylsilyl protons (δ0.22); vinylic proton (δ8.24); the N,N-dimethylamino protons (δ3.18); and the ribosyl protons (δ6.2–4.3).

In view of the susceptibility of these compounds to moisture, the catalytic reduction of compounds 34 was accomplished using special precautions to exclude all moisture from the catalyst and solvent as described later. Using an activated form of Raney nickel and 30–35 atm of hydrogen, the trimethylsilyl cyanohydrins were cleanly reduced and ring closed to afford the 6,7,8-trihydro-3-(2,3,5-tri-O-acetyl-β-D-ribofuranosyl)-v-triazolo [4,5-d] [1,3] diazepin-8-ol as a mixture of the trimethylsilyl ether and the free alcohol, compounds 35 and 36, respectively. A hydrolytic removal of the trimethylsilyl group of 35 was effected by stirring a solution of 35 and 36 in aqueous methanol for 2–3 hours.

Deprotection of the ribosyl moiety of 36, using methanolic ammonia, yielded the R and S diastereomers 4 and 37 as a mixture in 64% yield. A programmed gradient elution of water-methanol through a ODS-3 reverse phase column provided a separation of 4 and 37 (1:3, w/v). Compounds 4 and 37 are remarkably similar to their $^1$H NMR, $^{13}$C NMR (see Table III), and ultraviolet spectra. Compound 4 has been tentatively assigned the R configuration at C(8) based on the finding that it is a very tight-binding inhibitor of the enzyme. The R configuration at this carbon center is shared by similar tight-binding inhibitors of the enzyme.

TABLE III $^{13}$C—NMR Data for the Diastereomers 6,7,8-Tri-hydro-3-β-D-ribofuranosyl-v-triazolo[4,5-d] [1,3]diazepin-8(R,S)-ol Nucleosides 4 and 37.

| Carbon | 37$^a$ | 4 |
|---|---|---|
| C(5) | 150.30 | 150.30 |
| C(7) | 48.23 | 48.23 |
| C(8) | 64.14 | 64.02 |
| C(3a)$^b$ | 141.28 | 141.18 |
| C(8a) | 136.88 | 136.88 |
| C(1')$^c$ | 87.90 | 87.78 |
| C(2') | 73.27 | 73.27 |
| C(3') | 70.85 | 70.85 |
| C(4') | 85.28 | 85.28 |
| C(5') | 62.29 | 62.29 |

$^a$Chemical shifts are expressed in ppm downfield from Me$_4$Si. Values were measured relative to an internal DMSO standard and converted to the Me$_4$Si scale using (Me$_4$Si) = (DMSO) − 39.50 ppm. Concentration: 15 mg/0.3 ml DMSO-d$_6$. Temp ca. 27°.
$^b$Unambiguous assignment of the bridgehead signals was made from a three-bond $^{13}$C—H decoupling of the H(1') proton with the C(3a) carbon and a similar decoupling of the H(5) proton with the C(3a) carbon.
$^c$The chemical shift sequence for the carbons of the β-D-ribofuranosyl moiety have been well established for similarly substituted nucleosides.

The mixture of the R and S isomers of the 4,5,6-trihydro-1-(β-D-ribofuranosyl) pyrazolo [5,4-d] [1,3] diazepin-4-ol, (compounds 3 and 26), and the individual R and S isomers of the 6,7,8-trihydro-3-β-D-ribofuranosyl-v-triazolo [4,5-d][1,2] diazepin-8-ol, (compounds 4 and 37), were assayed as inhibitors of the enzyme adenosine deaminase (ADA). Using adenosine as a substrate for the purified enzyme, all compounds tested were found to be competitive inhibitors of ADA (See Table IV). In addition, compound 4 was found to be a potent tight-binding inhibitor of the enzyme.

TABLE IV

Inhibition of Adenosine Deaminase by Target Compounds

| X | Y | Compound | K$_i$ (μM) |
|---|---|---|---|
| N | C | 2, coformycin | 0.00012 |
| C | N | (3 + 26)$^a$ | 2 |
| N | N | 4 (R) | 0.002$^b$ |
| N | N | 37 (S) | 85 |

$^a$Unresolved mixture
$^b$Preliminary estimates based on conventional kinetic analysis.

Using a similar reaction sequence, one can prepare the 2'-deoxy derivative of 4(2-azacoformycin). An alternate route for the synthesis of 2'-deoxy-2-azacoformycin is

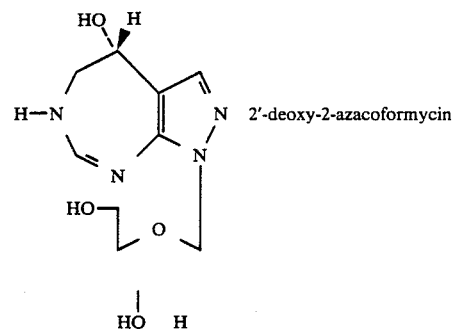

2'-deoxy-2-azacoformycin to block the 3',5'-hydroxyl groups followed by thioacylation of the 2'-hydroxyl group, subsequent removal of the group at the 2'-position and the blocking group from the 3',5'-hydroxyl groups to afford 2'-deoxy-2-azacoformycin.

In order to further illustrate the details of the short, facile sequence leading to the synthesis of the 3,4,5-trihydro-1,3-diazepin-5-ol moiety according to the present invention, the following EXAMPLE is presented of the overall total synthesis. In presenting this specific embodiment, it should be kept in mind that sequence is felt to be generally applicable to several ortho-aminoaldehydes. The mild nature of each of the steps in the schemes being exemplified lends applicability of the method to most parent heterocycles and suitably protected nucleosides. The only major functional requirement is the assemblance of an aldehyde group on a position ortho to an aldehyde on the parent ring. Compounds with the necessary functional groups may be isolated with relative ease under carefully controlled acidic conditions.

Further, under specific conditions, the moisture sensitive trimethylsilyl cyanohydrin nucleoside intermediates may be isolated and purified. These compounds may be chromatographed using anhydrous techniques which are to be described. Finally, a method for the catalytic reduction of the nitrile groups of our trimethylsilyl cyanohydrins under neutral conditions has been developed. Nickel boride, cobalt boride, or T-1 Raney nickel catalysts under 20–35 atm of hydrogen effected the reduction of the nitrile groups with a subsequent in situ annulation.

In performing the EXAMPLE, the following general methods and equipment were used. Melting points were taken on a Thomas-Hoover Unimelt capillary melting point apparatus and are uncorrected. Infrared (IR) spectra were determined on a Perkin-Elmer 281 spectrophotometer. Ultra-violet (uv) spectra were recorded on a Hewlett-Packard 8450A UV/Vis spectrophotometer. $^1$H nuclear magnetic resonance ($^1$H NMR) spectra were recorded for ca. 10% w/v solutions of the compounds on a Varian EM-360A (60 MHz) spectrometer or 1% w/v solutions of compounds on a WM Bruker (360 MHz) spectrometer operating in an FT mode. $^{13}$C nuclear magnetic resonance ($^{13}$C NMR) spectra were recorded for ca. 1% w/v solutions of the compounds on a WM Bruker (360 MHz) spectrometer operation in an FT mode and using a semi-micro 5 mm tube and probe.

Column and flash chromatography were performed using silica gel 60 (E. Merck, Darmstadt, West Germany; 70–230 mesh). Columns were packed with dry silica gel and then eluted with one void volume of the eluting solvent before a concentrated solution of the mixture in the eluting solvent was applied to the top of the column. Mixtures not readily soluble in the eluting solvent system were previously evaporated with a twofold (w/v) amount of silica gel 60, using an appropriate solvent. The mixture was then applied as a dry powder to the top of the column. Thin layer chromatography was performed using pre-scored SilicAR 7GF Analtech (Newark, Del.) silica gel (0.25 mm layer) plates. Nucleoside components were visualized with a Mineralight short wave (254 nm) uv lamp and further sprayed with a 10% aqueous solution of sulfuric acid to char these components upon heating on a hot plate. Low pressure chromatography was performed using the silica gel 60 columns: Lobar (E. Merck), size B (25×310 mm); size C (37×440 mm); and Michell-Miller (Ace Glass), size 22×300 mm; size 37×350 mm; and size 22×130 mm precolumn. An FMI Fluid Metering pump operating at 1.5–2.5 kg/cm$^2$ (20–35 lb/in$^2$) was used to elute components. Flow rates of 5.0–10.0 ml/min were commonly used. An Altex 125 Dual Wavelength UV (254 and 280 nm) detector with a preparative flow cell was used to detect uv-absorbing components. Chromatography solvents include the following: A, ethyl acetate; B, ethyl acetate-methylene chloride, 1:1; C, ethyl acetate-methylene chloride, 3:2; D, ethyl acetate-benzene, 9:1; E, ethyl acetate-water-n-propanol, 4:2:1, upper layer; F, ethyl acetate-methanol, 19:1; G, chloroform; H, chloroform-methanol, 40:1; I, acetonitrile-1M aq. ammonium chloride, 4:1, upper layer.

High performance liquid chromatography (HPLC) analyses and preparative separations were performed on a Varian Vista 54 series liquid chromatograph coupled with a Varian UV 50 variable wavelength detector. Analytical determinations were performed on a Varian Micro Pak (MCH-10, 4 mm×30 cm) ODS-18 reverse phase column. Preparative separations were performed on a Whatman Partisil (M-20, 10 mm×50 cm) ODS-3 reverse phase column.

All solvents and reagents were "reagent grade" unless otherwise noted. Reaction solvents were dried by distillation (tetrahydrofuran from LiALH$_4$; pyridine from BaO; p-dioxane from Na$^*$) or by storage over the appropriate activated Linde molecular sieves (dimethylformamide, acetonitrile, 4 Å; acetone, dichloromethane, and benzene 3 Å). All evaporations were routinely conducted at 30°–45° unless otherwise noted. Water aspirator vacuum (10–15 Torr) was used to evaporate low boiling (bp<ethanol) solvents and vacuum pump pressure (0.5–1.0 Torr) was used to evaporate higher boiling solvents.

Hydrogenations at low hydrogen pressure (1–5 atm H$_2$) were carried out using a Parr hydrogenation apparatus (Model 2911, Parr Instrument Co., Moline, Ill.) and a 500 ml bottle at room temperature. Hydrogenations at high hydrogen pressure (8–35 atm H$_2$) were carried out using a stainless steel reaction vessel (Model 4051, Parr) and glass sleeve. The contents of the sealed reaction vessel were heated by an oil bath and stirred with a magnetic stir bar and magnetic stirrer (with hot plate) combination.

1-O Acetyl-2,3,5-tri-O-benzoyl-$\beta$-D-ribose were purchased from Pfanstiehl Laboratories of Waukegan, Ill.

EXAMPLE

In order to synthesize 5-amino-1-methylpyrazole-4-carboxaldehyde, 6,5-amino-4-cyano-1-methylpyrazole (5, 10.0 g, 82 mmol) was dissolved in 70% aqueous acid (300 ml) with gentle warming. The light yellow solution was purged with a steady stream of nitrogen for 20 min. and then treated with T-1 Raney nickel (3 g, weighed wet). The mixture was stirred under 1 atm of hydrogen at room temperature for 72 hours. The solution was filtered through a bed of packed Celite (20 g) on a 250 ml sintered glass funnel and the catalyst bed was promptly washed with warm (70°) absolute ethanol (100 ml). The combined filtrates were evaporated to dryness in vacuo (water bath, 65°) to afford a yellow syrup. Repeated treatment of this syrup with cold water (6×50 ml) and an evaporation of each portion of water in vacuo afforded a thick slurry of crystalline material. This material was suspended in 100 ml of cold water and collected by filtration. The filtrate was evaporated by one-half of its volume to afford a second crop of crystals which was filtered and combined with the first crop. The filter cake was washed with cold water (20 ml) and then dried in a vacuum oven (50°, 0.1 Torr) over P$_2$O$_5$ for 18 hours to afford 7.5 g (73%) of compound 6 as yellow prisms. M.P. 158.5–159.5 (Lit. 148°–149°); $^1$H-NMR (DMSO-d$_6$): $\delta$9.60 (s, 1, CHO); 7.55 (s, 1, H(3)); 6.70 (br s, 2, NH$_2$, exch.); 3.53 (s, 3, CH$_3$). IR$\nu_{max}^{KBr}$: 1650 cm$^{-1}$ (CHO); 3320 cm$^{-1}$, 3420 cm$^{-1}$ (NH$_2$). UV$\lambda_{max}$ (nm), log$_{10}$ $\epsilon$): methanol, 284 (3.82), 241 (3.77); pH 1, 274, (3.76), 238 (3.75): pH 11, 284 (3.81), 243 (3.71).

In order to make 5-(N,N-Dimethylaminomethyleneamino)-1-methylpyrazole-4-carboxaldehyde, 10, the aldehyde 6 (5.0 g, 40 mmol) was suspended in anhydrous methylene chloride (50 ml) and treated with dimethylformamide dimethylacetal (DMFDMA, 5.9 ml, 44 mmol) under anhydrous conditions. The reaction was stirred for 3 hours at room temperature and then evaporated to dryness in vacuo to afford a light yellow oil. This oil was kept under vacuum pump pressure for 18 hours. Thin layer chromatograms of this material revealed compound 10 ($R_f$=0.35, solvent A) as the predominant product and compound 11 as a very minor product ($R_f$=0.45, solvent A). An aliquot of this mixture (0.5 g) was chromatographed on a Michell-Miller column (300 mm length) using a low pressure chromatography apparatus. The mixture was separated using solvent B as eluent and a flow rate of 6 ml/min, monitoring fractions by TLC (solvent A). Fractions containing compound 11 were pooled and evaporated to dryness in vacuo to afford 20 mg of a white solid which was unstable to moisture. M.P. 55°–57°; $^1$H -NMR (CDCl$_3$): δ9.75 (s, 1, CHO); 9.02 (s, 1, CH=N); 7.90 (s, 1, H$_3$); 4.00 (s, 3, CH$_3$O); 3.80 (s, 3, N-CH$_3$). UV$_{max}$ (nm), (log$_{10}$ ε): methanol, 274 (3.80). Anal. Calcd for C$_7$H$_9$N$_3$O$_2$: C, 50.30; H, 5.42; N, 25.14. Found: C, 50.21; H, 5.47; N, 25.74. Fractions containing compound 10 were pooled separately and evaporated to dryness in vacuo to afford 420 mg of a waxy white solid. M.P. 47°–51°; $^1$H -NMR (CDCl$_3$): δ9.42 (s, 1, CHO); 8.53 (s, 1, cH=N); 7.70 (s, 1, H$_3$); 3.53 (s, 3, N(1)-CH$_3$); 3.00, 2.92 (s, s; 3, 3; N,N-dimethyl). UV$\nu_{max}$ (nm), (log$_{10}$ ε): methanol, 318 (3.89), 234 (4.42. Anal. Calcd for C$_8$H$_{12}$N$_4$O: C, 53.32; H, 6.71; N, 31.09. Found: C, 53.56; H, 6.58; N, 30.97. Elemental analyses (C, H, N) of the crude reaction mixtures were found to be well within experimental limit as calculated for the predominant product, compound 10. Therefore, these mixtures were routinely used for the next step without prior separation of the two compounds 10 and 11. The yield of crude product was 7.2 g (100%).

In preparing 5-(N,N-Dimethylaminomethyleneamino)-4-(cyano[trimethylsiloxy]methyl)-1-methylpyrazole 12 and 5-Methoxymethyleneamino-4-(cyano[trimethylsiloxy]methyl)-1-methylpyrazole 13, the mixture composed of compounds 10 and 11 (7.2 g, 40 mmol as calculated for compound 10 was dissolved in trimethylsilyl cyanide (TMSCN, 6.0 ml, 56 mmol) with gentle warming in a scrupulously dried 50 ml round bottom flask. While maintaining a dry nitrogen atmosphere, dry powdered zinc chloride (30 mg) was introduced and the flask sealed with a rubber septum. The reaction mixture was stirred for 30 minutes at room temperature and then additional TMSCN (2 mL) was added, using a syringe. The yellow cake was broken up and triturated with anhydrous hexane (3×25 ml) and then filtered to give 10.0 g (90%) of a mixture of 12 and 13 as a brilliant yellow solid. Further purification of this cyanohydrin mixture was effected using a Merck Lobar silica gel "B" column which had been previously eluted with a solution of 2,2-dimethoxypropane in ethyl acetate (170 ml; 3%, v.v). Solvent system B was used as eluent and a flow rate of 5.0 ml/min was maintained throughout the separation. The eluates were monitored using an Atex UV detector (254 nm, 280 nm) and TLC (solvent system B) analysis of each fraction. The mixture of trimethylsilyl cyanohydrins, 12 and 13, were first to elute and fractions 10–18 (7 ml/fraction) were pooled and evaporated in vacuo to give nearly colorless rosettes, 7.5 g (70.3%). M.P. 128°–130°. This material was susceptible to moisture and was kept in a vacuum desiccator over P$_2$O$_5$ during storage. $^1$H-NMR (CDCl$_3$): δ8.00 (s, 1, CH=N); 7.43 (s, 1, H$_3$); 5.55 (s, 1, methine); 3.70 (s, 3, CH$_3$); 3.10 (s, 6, N,N-dimethyl); 0.2 (s, 9, trimethylsilyl). The methoxy protons of compound 13 were just discernible at δ4.00 in the spectrum of this mixture. UVλ$_{max}$(nm), (log$_{10}$ ε): methanol, 265 (4.03), 243 (4.06). A sample (500 mg) of the mixture of trimethylsilyl cyanohydrins was recrystallized from 50% aqueous ethanol (10 ml) to yield a sample of the cyanohydrin 14 for analysis. Anal. Calcd for C$_9$H$_{13}$N$_5$O.0.25 H$_2$O: C, 51.06; H, 6.38: N, 33.10. Found: C, 51.23; H, 6.46; N, 33.01. $^1$H-NMR (CDCl$_3$): δ8.00 (s, 1, CH=N); 7.55 (S, 1, H(3)); 6.53 (d, 1, —OH, exch.); 5.33 (d, 1, H(4)); 3.70 (s, 3, N—CH$_3$); 3.23 (s, 6, N,N-dimethyl). The individual formylated aldehydes, compounds 10 and 11 were each treated with TMSCN/ZnCl$_2$ and each aldehyde gave a different and distinct trimethylsilyl cyanohydrin product. These products were each purified using low pressure chromatography techniques described earlier for the crude mixture. The trimethylsilyl cyanohydrins obtained from these reactions were characterized using $^1$H-NMR spectra and by comparison of these spectra with the spectrum taken of the mixture obtained after low pressure chromatographic purification of the crude reaction mixture. The $^1$H-NMR (CDCl$_3$) spectrum of compound 13 exhibited: δ8.30 (S, 1, CH=N); 7.50 (s, 1, H(3)); 5.40 (s, 1, methine); 4.00 (s, e, CH$_3$O); 3.75 (s, 3, N—CH$_3$); 0.20 (s, 9, trimethylsilyl). The $^1$H-NMR Spectrum of compound 12 was identical to the spectrum obtained from the mixture of compounds 12 and 13, but without the background peaks observed for the minor component.

4,5,6-Trihydro-1-methylpyrazolo [5,4-d] [1,3] diazepin4(R,S)-ol, 9: a 500 ml Parr stainless steel reaction vessel fitted with a scrupulously dried glass sleeve was charged with a solution of the trimethylsilyl cyanohydrins compounds 12 and 13; 0.25 g, 0.89 mole as calculated for compound 12 in dry p-dioxane (40 ml). This solution was purged with dry nitrogen for 20 min. Nickel boride (NiB$_x$) Catalyst (0.30 g, weighed wet) was repeatedly washed with dry p-dioxane (4×10 ml) by decantation and the final suspension was added to the purged solution of trimethylsilyl cyanohydrins. The stainless steel vessel was sealed, flushed with hydrogen (3 c 40 psi), filled with 125 psi of hydrogen, and then heated to 110° over a magnetic stirrer. An equilibrium pressure of 140 psi hydrogen was maintained for 19 hours. After this time, the reaction mixture was filtered through a bed of packed Celite (6 g) on a 60 ml sintered glass funnel and the catalyst bed was promptly washed with methanol (3×15 ml). The pH of the filtrates was adjusted to 5 with 7.5 ml of 0.1N aqueous acetic acid and the amber solution warmed (55°) on a steam bath for two hours. Subsequently, the mixture was evaporated to dryness in vacuo to afford a dark oil. The oil was repeatedly dissolved in absolute ethanol (3×15 ml) and each portion was evaporated to dryness in vacuo to afford a yellowish residue. Trituration of this residue with methylene chloride (5 ml) gave a white amorphous solid which was collected by filtration. The solid was dissolved in water (5 ml) and then lyophilized to afford 95 mg (65.8%) of 9 as a white hygroscopic solid. M.P. 230° (dec.). $^1$H-NMR (360 MHz) (DMSO-d$_6$): δ7.62 (m, 1, N-H, exch.); 7.06 (s, 1, H(3)); 6.86 (d, 1, H(7), $J_{7,6}$=4.6 Hz); 5.07 (d, 1, —OH, exch., J=5.5 Hz); 4.58 (sextet, 1, H(4), J=6.1, 5.5, 2.1 Hz); 3.54 (s, 3, N-CH$_3$); 3.22 (octet, 1, H(5a), J = 12.8, 2.6, 2.1 Hz); 3.02 (octet, 1, H(5b), J=12.8, 6.1, 2.6 Hz). UVλ$_{max}$ (nm), (Log$_{10}$ ε): methanol, 275 (4.01); pH 1, 241 (3.84; pH 11, 274 (4.06). Anal. Calcd for C$_7$H$_{10}$N$_4$O: C, 50.58; H, 6.07; N, 32.73. Found: C, 50.82; H, 6.15; N, 33.00.

To further illustrate the procedures of Scheme II, a rapidly stirred suspension of 1-deoxy-1-hydrazinyl-2,3-O-isopropyliden-D-ribose (24.0 g, 0.16 mmol) in anhydrous acetone (150 ml) was treated with a catalytic amount of concentrated sulfuric acid (0.5 ml) under anhydrous conditions and at room temperature. The rapidly stirred suspension was immediately treated with a dropwise addition of a solution of 2,2-dimethoxypropane (49 ml, 0.40 mol) in anhydrous acetone (30 ml, dry) over a period of 0.5 hour. When the last trace of solid ribose was dissolved (45 min from the addition of acid), the reaction was quenched with dry, powdered sodium carbonate (2.2 g) and the reaction mixture was allowed to stir for an additional hour. The heterogeneous mixture was filtered, the inorganic bed was washed with additional anhydrous acetone (50 ml), and the combined filtrates were evaporated in vacuo to afford a light yellow viscous oil. This oil was chromatographed on a silica gel (500 g) column (6×30 cm). The column was first eluted with solvent G (2 l) to elute some very fast running side products. Additional elution with solvent H (2.5 l) eluted with 2,3-O-isopropylidene-D-ribose ($R_f$=0.53, solvent A). The separation was monitored by TLC and the fractions containing this material were pooled and evaporated in vacuo to afford a colorless syrup, 23.8 g (78%). $^1$H-NMR (DMSO-$d_6$): $\delta$6.33 (m, 2, —OH, exch.); 5.20 (s, 1, H(1)); 4.75 (d, 1, H(2), $J_{2,3}$ 6.0 Hz); 4.40 (d, 1, H(3), $J_{3,2}$ 6.0 Hz); 4.00 (t, 1, H(4), $J_{4,5}$=7.0 Hz); 3.45 (d, 2, H(5), $J_{5,4}$ 7.0 Hz); 1.35, 1.27 (s, s: 3,3: isopropylidene). $[\alpha]_D^{25}$=−37 (c, 0.53, acetone). All physical data was identical with literature values for 2,3-O-isopylidene-D-ribose.

A solution of 2,3-O-isopropyliden-D-ribose (29.2 g, 0.15 mol) in absolute methanol (200 ml) was treated with a solution of anhydrous hydrazine (40.3 g, 1.5 mol, 97% reagent grade) in absolute methanol (100 ml) dropwise over a period of 15 min and at room temperature. The nearly colorless solution was stirred at room temperature and under anhydrous conditions for 18 hours. The solution was filtered and the filtrate was evaporated in vacuo to afford a colorless syrup. The syrup was repeatedly treated with absolute methanol (5×100 ml) and each portion was individually evaporated in vacuo to remove the bulk of the excess hydrazine. The syrup was then momentarily warmed (70°) under vacuum pump pressure (0.1 Torr) and then kept at this pressure and room temperature for storage. The yield was 34.9 g (theoretical yield is 31.4 g) which includes trapped hydrazine and water. This material was used without further purification for the next step. $R_f$=0.25, 0.10, solvent A. $^1$H-NMR (DMSO-$d_6$): $\delta$7.00 (d, 1, H(1), $J_{1,2}$=3 Hz); 6.25 (br s, 3, NHNH$_2$, exch.); 1.30, 1.20 (s,s; 3,3; isopropylidene), identical with literature values. This spectrum also exhibited a larger water signal at 4.9. This product deteriorates under continued storage and consequently should be used within 48 hours after preparation.

To synthesize 5-Amino-4-cyano-1-(2,3-O-isopropylidene-$\beta$-D-ribofuranosyl)pyrazole, 18, a solution of the hydrazinyl sugar (16, 43.0 g, 0.21 mol) in absolute ethanol (300 ml) was purged with a steady stream of nitrogen for 30 minutes. A similarly purged solution of ethoxymethylene malononitrile (17, 27.8 g, 0.23 mol) in absolute ethanol (150 ml) was added dropwise to the rapidly stirred solution of 16 at room temperature for 1 hour. The solution was stirred under nitrogen for an additional 30 minutes and heated at reflux for 12 hours. The reaction did not proceed further after this time (vide infra TLC analysis). A single nucleoside product appeared on TLC as an UV absorbing, charring (10% aqueous sulfuric acid spray) spot ($R_f$=0.55, solvent system D). The orange solution was cooled to room temperature, filtered and evaporated in vacuo to yield a solid orange foam. This material was dissolved in ethyl acetate (100 ml) and then treated with silica gel (75 g). The mixture was evaporated to dryness in vacuo and the powder which resulted was applied to the top of a silica gel (500 g) column (6×30 cm, dry packed). The column was eluted with solvent system C (2.5 l) but the first fractions (fractions 33–34, 55 ml, fraction) containing the nucleoside were contaminated with an unidentified sugar fraction and were pooled separately. Fractions 45–70 contained the pure nucleoside product; these fractions were pooled and evaporated to yield 12.0 g of a crisp white foam. Chromatography of the impure fractions on a similar column of silica gel (200 g), using solvent system C yielded an additional 5.1 g of nucleoside 18 for a total yield of 28.9%. The foams from both separations were triturated separately with cold anhydrous ether (10–20 ml) to yield amorphous solids which were collected by filtration. These solids were combined and subsequently crystallized from boiling ether to afford 15.5 g of colorless plates. M.P. 116°–117°. $^1$H-NMR (DMSO-$d_6$): $\delta$7.72 (S, 1, H(3)); 6.90 (m, 2 NH$_2$, exch.); 6.15 (S, 1, H(1')); 1.50, 1.30 (s,s; 3,3; isopropylidene, $\Delta\delta$=12 Hz). UV$\lambda_{max}$(nm), (log$_{10}$ $\epsilon$): methanol, 288 (2.75), 236 (4.02); pH 1, 233 (4.03); pH 11, 235 (4.05). IR$\lambda_{max}^{KBr}$: 220 cm$^{-1}$ (CN). Anal. Calcd for C$_{12}$H$_{16}$N$_4$O$_4$: C, 51.43; H, 5.75; N, 19.99. Found: C, 51.20; H, 5.63; N, 19.98.

In preparing 5-Amino-1-(2,3-O-isopropylidene-$\beta$-D-ribofuranosyl)-pyrazole-4-carboxaldehyde, 19, compound 18 (5.0 g, 17.7 mmol) was dissolved in pyridine-acetic acid-water (50 ml, 1:1:1, v/v) and the solution was purged with a steady stream of nitrogen for 20 min. T-1 Raney nickel (1.5 g, weighed wet) was added to the solution and the mixture was shaken under hydrogen (45 psi) on a Parr hydrogenation apparatus at room temperature for 10 hours. The mixture was then filtered through packed Celite (15 g) on a 60 ml (4.5 cm internal diameter) sintered glass funnel and the catalyst bed was promptly washed with water (100 ml) and ethanol (3×50 ml). The combined filtrates were evaporated in vacuo to afford a thick green syrup. This syrup was treated with ethanol (3×50 ml) and toluene (4×50 ml) and each portion was individually evaporated to dryness in vacuo to yield a green residue. This residue was dissolved in ethanol (50 ml), treated with silica gel (10 g) and the mixture evaporated in vacuo to afford a dark powder. The silica gel powder was applied to the top of a silica gel (30 g) column (3×4.5 cm) in a 60 ml sintered glass funnel. The aldehyde 19 was eluted from the column with solvent (200 ml) and the eluates were evaporated to dryness in vacuo (water bath, 40°) to afford a light yellow syrup. This syrup was readily crystallized on trituration with dry diethyl ether (10 ml) to yield 3.5 g (69.3%) of 19 as analytically pure yellow prisms. M.P. 134°–135°. $^1$H-NMR (CDCl$_{3;l}$): $\delta$9.65 (s, 1, CHO); 7.70 (s, 1, H(3)); 6.10 (br m, 2, NH$_2$, exch.); 1.50, 1.39 (s,s; 3,3; isopropylidene, $\Delta\delta$=12 Hz). UV$\lambda_{max}$(nm), (log$_{10}$ $\epsilon$): methanol, 284 (3.95); pH, 284 (3.93), 236 (3.86); pH 11, 284 (3.95), 237 (3.92), 222 (3.87). Anal. Calcd for C$_{12}$H$_{17}$N$_3$O$_5$: C, 50.88; H, 6.04; N, 14.83. Found: C, 51.04; H, 6.01, N, 14.67.

In preparing 5-Amino-1-(2,3,5-tri-O-acetyl-$\beta$-D-ribofuranosyl)pyrazole-4-carboxaldehyde, 21, a solution of compound 19 (10.0 g, 35.5 mmol) in a mixture of methanol-water (150 ml, 2:1, v/v) was treated with DOWEX 1×4 (H+) ion exchange resin (8 ml, wet). Aqueous 1N hydrochloric acid (20 ml) was added to this solution and the mixture was stirred at room temperature for 48 hours. During the course of the reaction, a yellow precipitate formed, corresponding to the deblocked aldehyde. The solid material, consisting of the insoluble aldehyde and the spent resin, was collected by filtration and washed with cold absolute ethanol (30 ml). The material was then dried in a vacuum oven (35°, 10 Torr) over $P_2O_5$ for 18 hours. The resulting fluffy yellow material was suspended in anhydrous pyridine (100 ml). This suspension was then treated with acetic anhydride (15 ml) and stirred under anhydrous conditions at room temperature for 12 hours. The mixture was filtered through fluted filter paper onto crushed ice (100 ml), the resin bed was washed with chloroform (3×30 ml), and the combined filtrates were stirred at 0° for 20 min. The filtrates were extracted with chloroform (2×200 ml) and the combined chloroform extracts were successively washed with cold saturated aqueous sodium bicarbonate (3×50 ml), cold aqueous 1N HCl (2×50 ml), and cold water (50 ml). The chloroform layer was dried over anhydrous magnesium sulfate (20 g), filtered, and evaporated to dryness in vacuo to afford a thick yellow syrup. This syrup was treated with toluene (2×50 ml) and each portion was individually evaporated to dryness in vacuo to afford a light yellow amorphous solid. This solid was triturated with warm ethanol (40°, 30 ml), and the mixture was cooled in an ice bath, and the solid which separated from solution was collected by filtration. The filter cake was washed with cold ethanol (20 ml) followed by air drying of the cake to afford 8.0 g (61.4%) of compound 21 as a light yellow solid. M.P. 134°–345°. $^1$H-NMR (CDCl$_3$): δ9.70 (s, 1, CHO); 7.70 (s, 1, H(3)); 6.25 (m, 2, NH$_2$, exch.); 5.85 (s, 1, H(1′)); 2.20, 2.10 (s,s,; 6.3; COCH$_3$), UVλ$_{max}$(nm), (log$_{10}$ ε): methanol, 264 (2.45), 286 (3.94); pH 1, 285 (3.94), 236 (3.87); pH 11, 284 (3.89), 236 (3.87). Anal. Calcd for $C_{15}H_{19}N_3O_8$: C, 45.78; H, 5.18; N, 11.38. Found: C, 45.93; H, 5.25; N, 11.42.

To synthesize 5-(N,N-Dimethylaminomethylenamino)-1-(2,3,5-tri-O-acetyl)-β-D-ribofurnaosyl)-pyrazole-4-carboxaldehyde, 22, compound 21, (7.61 g, 20.5 mmol) was dissolved in anhydrous methylene chloride (30 ml) and the solution was treated with dimethylformamide dimethylacetal (Aldrich Chem. Co., DMFDMA, 6.8 ml, 51.3 mmol) under anhydrous conditions and at room temperature. The mixture was stirred for 2 hours at room temperature and then evaporated to dryness in vacuo to yield a brilliant yellow oil. The oil was placed under vacuum pump pressure (0.1 Torr) for 3 hours and then dissolved in absolute ethanol (50 ml). The solution was kept at 5° for 36 hours to complete crystallization. The crystalline material which had separated from solution was collected by filtration and the crystalline cake was washed with cold ethanol (120 ml) to afford 5.6 g (66.0%) of material. This material contains a large predominance of compound 22 (R$_f$=0.55, solvent A) over the methoxy-formylated compound (R$_f$=0.61, solvent A) as a minor impurity. $^1$H-NMR (CDCl$_3$): δ9.68 (s, 1, CHO); 8.60 (s, 1, CH═N); 7.98 (s, 1, H(3)); 6.20 (m, 1, H(1′)); 3.15, 3.03 (s,s; 3,3; N,N-dimethyl); 2.10, 2.00 (d,d; 6,3; COCH$_3$), UVλ$_{max}$(nm), (log$_{10}$ ε): methanol, 322 (4.03), 234 (4.57); pH 1, 217 (4.45); pH 11, 232 (4.79). Anal. Calcd for $C_{18}H_{23}N_4O_8$: C, 50.94; H, 5.69; N, 13.20. Found: C, 50.69; H, 5.69; N, 13.20. The $^1$H NMR spectrum of the mixture also exhibited a signal for the methoxy protons of the minor product at 4.00 which was just discernible. Consequently, this material was estimated to contain 2–3% of this impurity as in the case of the model compounds 10 and 11. This impurity did not significantly alter the elemental analysis as calculated for the major component, compound 22. Routinely, these mixtures were not separated but used as such for the next synthetic step.

To make 5-(N,N-Dimethylaminomethyleneamino)-4-(cyano[trimethylsiloxy]methyl)-1-(2,3,5-tri-O-acetyl)-β-D-ribofuranosyl)pyrazole, 23, a scrupulously dried 100 ml round bottom flask containing the nucleoside 22 (5.22 g, 12.3 mmol) was sealed with a septum and flushed for 20 min. With nitrogen, using a dual set of needles. Trimethylsilyl cyanide (TMSCN, 7.8 mL, 61.5 mmol) was added via a syringe, keeping rigorous anhydrous conditions. The mixture was warmed slightly to effect dissolution and then cooled to 5° in an ice bath. A solution of BF$_3$.OEt$_2$ in ether (1 ml, 1:1, v/v) was added to the frozen mixture via a syringe and the flask was then allowed to slowly thaw by removal of the ice bath. Subsequently, the reaction was allowed to warm to room temperature and then stirred for 14 hours under a positive pressure of nitrogen. The reaction was cooled to 5° and an additional 1 ml of dilute BF$_3$.OEt$_2$ was added. The very dark solution was evaporated to dryness in vacuo and the residue which resulted was kept under vacuum pump pressure (0.1 Torr) for 3 hours. The residue solidified upon standing under vacuum and was triturated with cold absolute ethanol (20 ml). The solid which remained separated from solution was collected by filtration and the filter cake was washed with an additional portion of cold absolute ethanol (10 ml). The solid was dried in vacuo at room temperature to yield 2.75 g of an off-white powder M.P. 186°–188°. The mother liquors were immediately evaporated to dryness in vacuo. The resulting syrup was dissolved in ethyl acetate (5 ml) and this solution chromatographed on a Michell-Miller column (300 mm length) and similar precolumn (100 mm length). Both columns had been previously treated with a solution of 2,2-dimethoxypropane in ethyl acetate (200 ml, 3%, v/v) to remove all traces of water. A low pressure chromatography apparatus was used with solvent B (650 ml) as eluent and maintaining a flow rate of 5 ml/min. The progress of the separation was monitored with an Altex Uv detector (254 nm, 280 nm) and TLC analysis of each fraction. A total of three 150 ml fractions collected, the second of which contained all of the product with R$_f$=0.65, solvent A. This fraction was evaporated in vacuo to afford an additional 0.68 g of compound 23 as a thick syrup. The combined yield of products was 53%. $^1$H-NMR(CDCl$_3$): δ8.03 (s, 1, CH═N); 7.35 (s, 1, H(3)); 6.20 (d, 1, H1′), J$_{1',2'}$=2.0 Hz); 3.10 (s, 6, N, N-dimethyl); 2.10 (s, 9, COCH$_3$); 0.24 (s, 9, trimethylsilyl). UVλ$_{max}$(nm), (log$_{10}$ ε): methanol, 273 (4.04). Anal. Calcd for $C_{22}H_{35}N_5O_8Si$: C, 50.46; H, 6.34; N, 13.38. Found: C, 50.53; H, 6.50; N, 13.47. The methoxy protons of the minor formylated product were just discernible in the $^1$H-NMR spectrum at 4.0. Consequently, this material was estimated to contain 2–3% of this impurity and it did not significantly alter the elemental analysis as calculated for the major component, compound 23.

To make 4,5,6-Trihydro-1-(2,3,5-tri-O-acetyl-β-D-ribofuranosyl) pyrazolo [5,4,-d] [1,3] diazepin-4(R,S), ol, 25, a 500 ml Parr stainless steel reaction vessel fitted with a scrupulously dried glass sleeve and containing a solution of the trimethylsilyl cyanohydrin (23, 1.0 g, 1.90 mmol) in anhydrous p-dioxane (40 ml) was purged with a steady stream of nitrogen for 20 min. T-1 Raney nickel (2.0 g, weighed wet) was washed with p-dioxane (4×10 ml) by decantation and the final suspension was added to the solution of nucleoside 23. The stainless steel vessel was sealed and then filled with 400 psi of hydrogen. The equilibrium pressure of 460 psi of hydrogen and 100° was maintained for 18 hours. The reduction mixture was filtered through packed Celite (12 g) on a 60 ml (4.5 cm internal diameter) sintered glass funnel and the catalyst and Celite bed was promptly washed with warm ethanol (60 ml). The combined filtrates were evaporated in vacuo to yield a colorless foam. This foam was dissolved in methanol (15 ml) and treated with aqueous 0.1N acetic acid (2 ml). The mixture was warmed to 50° in a water bath while being vigorously stirred for 30 min. The mixture was cooled, evaporated to dryness in vacuo and then successively treated with ethanol (2×20 ml) and toluene (2×20 ml) and each portion was individually evaporated in vacuo to yield a colorless residue. The residue was triturated with cold thyl acetate (10 ml) and the precipitate which separated from solution was collected by filtration. The filter cake was washed with cold ethyl acetate (5 ml) and then dried in a vacuum oven 50°, 10 Torr) for 12 hours to afford 380 mg (47%) of compound 25 as an amorphous white powder. M.p. 209°-210°. This material is a mixture of R and S diastereomers at C(4) which is reflected in the duplicate $^1$H-NMR signals for the H(3), H(7), and COCH$_3$ Protons. $^1$H-NMR (360 MHz) (DMSO-d$_6$): δ7.40, 7.41 (2s, 1, H(3)); 6.58, 6.42 (2d, 1, H(7), $J_{7A,N-H}$=4 Hz, $J_{7B,N-H}$=4 Hz; 6.28 (br s, 1, H(1')); 3.43-3.26 (m, 2, H(5)); 2.10-2.00 (6s, 9, COCH$_3$), UVλ$_{max}$(nm), (log$^{10}$ ε): methanol, 279 (3.99); pH 1, 264 (3.87), 234 (3.72); pH 11, 277 (4.07), 235 (3.83) Anal. Calcd for $C_{17}H_{22}N_4O_8$: C, 49.76; H, 5.40; N, 13.65. Found: C, 49.56; H, 5.52; N, 13.50.

To synthesize 4,5,6-Tihydro-1-(β-D-ribofuranosyl)-pyrazolo [5,4-d]-[1,3] diazepin-4(R,S)-ol,3 and 26, a mixture of the R and S diastereomers of 25 (0.15 g, 0.36 mmol) in methanolic sodium methoxide (5.75 ml, 0.13N) was stirred at room temperature for 1 hour. The pH of the solution was adjusted to 7 with DOWEX 1×4(H+) ion exchange resin and the mixture was stirred at room temperature for an additional 10 min. The solution was filtered, the resin bed was washed with additional methanol (10 ml) and the combined filtrates were evaporated to dryness in vacuo to yield a colorless gum. The gum was crystallized from warm (50°) ethanol (2 ml), and the crystalline material which had separated from solution was collected by filtration. This material was dried in a vacuum oven (50°, 10 Torr) for 12 hours to afford a mixture (90 mg, 86%) of compounds 3 and 26 as a white crystalline powder. M.P. 185°-187°. $^1$H-NMR (360 MHZ) (DMSO-d$_6$): δ7.82 (br s, 1, N-H, exch.); 7.28 (s, 1, H(3)); 6.97 (d, 1, H(7), $J_{7,6}$=2.8 Hz): 6.03 (d, 1, H(1'), $J_{1',2'}$=3.9 Hz); 4.66 (m, 1, H(4)): 3.30-3.10 (m, 2, H(5)). UVλhd max(nm), (log$^{10}$ ε): methanol, 278 (3.95), 241 (3.60); pH 1, 263 (3.82); 235 (3.77); pH 11, 277 (3.9), 238 (3.66). Anal. Calcd for $C_{11}H_{16}N_4O_5$: C, 46.48; H, 5.67; N, 19.71. Found: C, 46.24; H, 5.78; N, 19.47. For data on $^{13}$C-NMR See Table II. HPLC chromatography of this mixture, using several programmed gradient elutions of methanol-water (as described later for compounds 4 and 37) did not resolve the R and S mixture contained in this product.

To prepare 5-Amino-1-(2,3,5-tri-O-acetyl-β-D-ribofuranosyl)-v-triazole-4-carboxamide, 30, dimethylformamide (300 ml) was added to a cold (0°) solution of potassium hydroxide (6.40 g, 0.11 mol) in water (50 ml) and the solution stirred at this temperature for 10 min. Cyanoacetamide (9.53 g, 0.11 mol) was added to this solution and the mixture was stirred at 0° until all solid material disappeared. To this solution was added 1-deoxy-1-azido-2,3,5-tri-O-benzoyl-β-D-ribofuranose (28, 36.8 g, 76 mmol) in one portion and the reaction was stirred at −5° on a Stir-Kool apparatus for 14 hours. The amber solution was evaporated in vacuo (water bath 80°) to afford an orange semi-solid. This material was successively dissolved in absolute ethanol (2×50 ml) and toluene (3×50 ml) and each portion was individually evaporated to dryness in vacuo to afford a thick orange gum. The gum was then dissolved in anhydrous methanol (150 ml) and the solution treated with methanolic sodium methoxide (1N, 25 ml). This solution was stirred at room temperature under anhydrous conditions for 6 hours. The amber solution was treated with DOWEX 1×4(H+) ion exchange resin (approximately 35 ml wet resin) to bring the pH to 6. The solution was filtered, the resin bed was washed with an additional 50 ml of methanol, and the combined filtrates were evaporated to dryness in vacuo (water bath 80°) to yield an orange gum. The gum was repeatedly triturated with ethyl acetate (6×50 ml) and each portion was in turn decanted until the gum solidified to a tan amorphous solid. The solid was collected by filtration, dried in a vacuum oven (50°, 10 Torr) for 6 hours. The solid was dissolved in anhydrous pyridine (120 ml) and acetic anhydride (50 ml). The mixture was stirred under anhydrous conditions and at room temperature for 18 hours and then filtered through a shallow bed of packed Celite (15 g) in a 250 ml (6.5 cm internal diameter) sintered glass funnel. The Celite bed was washed with fresh pyridine (50 ml) and the combined filtrates were evaporated to dryness in vacuo to yield a brown gum. The gum was treated with a solution of ethyl acetate-methanol (50 ml; 1:1, v/v) and stirred at room temperature for a few minutes. The mixture was further cooled in an ice bath and the material which had crystallized after 30 min. at this temperature was collected by filtration. The off-white crystalline material was washed with cold methanol (2×50 ml) and air dried. The off-white crude product (15.5 g, 53% yield, M.P. 168°-170°) was chromatographically pure ($R_f$ 0.42, solvent A). Analytically pure material was obtained by recrystallization of this product from boiling ethanol (400 ml) to yield white needles, 11.8 g (40.8%), M.P. 175°-176°. A second recrystallization did not alter the melting point of this product. $^1$H-NMR(DMSO-d$_6$): δ7.55 (m, 2, CONH$_2$, exch.); 6.70 (br s, 2, NH$_2$, exch.); 6.25 (d, 1, H(1'), $J_{1',2'}$=3 Hz); 2.10, 1.97 (s, s; 6, 3; COCH$_3$). UVλ$_{max}$(nm), (log$^{10}$ ε): methanol, 259 (3.96), 236 (4.02); pH 1, 261 (4.02); 233 (4.11); pH 11, 252 (3.93), 236 (3.89). Anal. Calcd for $C_{14}H_{19}N_5O_8$: C, 43.64; H, 4.96; N, 18.17. Found: C, 43.58; H, 4.73; N, 18.35. A small sample of this material was dissolved in excess methanolic ammonia (saturated at 0°) and the solution stirred at room temperature for 8 hours. The solvent was removed in vacuo and the resulting residue was crystallized from methanol to obtain a product which was identical (M.P, UV, $^1$H-NMR) with the nucleoside reported in the literature as 5-amino-1-β-D-ribofuranosyl-v-triazole-4-carboxamide, 29.

To prepare 5-Amino-4-cyano-1-(2,3,5-tri-O-acetyl-β-D-ribofuranosyl)-v-triazole, 31, a suspension of the nucleoside 30 in anhydrous chloroform (200 ml) and triethylamine (40 ml) was treated dropwise with a solution of phosphorous oxychloride (5.4 ml, 52 mmol) in 50 ml of anhydrous chloroform over a period of 10 min. The heat generated from this addition caused all solid material to dissolve (final temperature 45°) and the resulting grey solution was stirred at 40° for 12 hours. The solution was poured onto crushed ice (150 ml) and stirred cold for 20 min. The chloroform layer was separated and washed successively with cold water (50 ml), cold aqueous 0.1N HCl (2×50 ml), and cold water (50 ml). The chloroform was dried over anhydrous magnesium sulfate (15 g), filtered, and evaporated in vacuo to afford a brown foam. This foam was dissolved in ethyl acetate (50 ml) and the solution was applied to the top of a shallow bed (6.5×2 cm) of silica gel (40 g) in a 250 ml sintered glass funnel. The compound 31 was eluted using solvent A (350 ml). The eluates were evaporated in dryness in vacuo to yield an orange foam, 6.5 g (68%). $R_f$=0.78, solvent A. $^1$H-NMR (DMSO-d$_6$): δ7.48 (m, 2, NH$_2$, exch.); 6.28 (d, 1, H(11), $J_{1',2'}$=3 Hz); 2.10, 1.95 (s, s; 6, 3: COCH$_3$), IR(thin film) $_{max}$: 2220 cm$^{-1}$ (CN). UVλ$_{max}$(nm), (log$^{10}$ ε): methanol, 255 (3.75), 230 (3.94); pH 1, 255 (3.70), 228 (3.90); pH 11, 254 (3.80), 233 (3.89). Anal. calcd for C$_{14}$H$_{17}$N$_5$O$_7$.0.5H$_2$O: C, 44.58; H, 5.05; N, 18.27. Found: C, 44.58; H, 4.82; N, 18.61.

To make 5-(N,N-Dimethylaminomethyleneamino)-1-(2,3,5-tri-O-acetyl-β-D-ribofuranosyl)-v-triazole-4-carboxaldehyde, 33, the nucleoside 31 (3.60 g, 9.57 mmol) was dissolved in a mixture of pyridine-acetic acid-water (100 ml; 2:1:1, v/v) in a Parr hydrogenation bottle (500 ml). The solution was purged with a steady stream of nitrogen for 20 min and then treated with T-1 Raney nickel (3.0 g, weighed wet). The mixture was shaken under hydrogen (45 psi) on a Parr hydrogenator for a total of 3 hours. The reaction mixture was filtered through packed Celite (18 g) on a 60 ml (4.5 cm internal diameter) sintered glass funnel and the catalyst bed was promptly washed with absolute ethanol (50 ml). The combined filtrates were evaporated to dryness in vacuo (water bath=50°) to yield a dark brown syrup. This syrup was treated with toluene (3×50 ml) and absolute ethanol (3×50 ml) and each portion was individually evaporated to dryness in vacuo to yield a dark brown gum. Alternatively, the dark brown syrup obtained by evaporation of the pyridine-acetic acid-water was dissolved in cold ethyl acetate (250 ml) and filtered. The filtrate was then washed successively with cold water (50 ml), cold saturated aqueous sodium bicarbonate solution (2×50 ml), cold aqueous 1N HCl (2×50 ml), and cold water (50 ml). The organic layer was dried over anhydrous magnesium sulfate (25 g), filtered, and evaporated in vacuo to afford a thick brown gum. The gum obtained from either method (containing the crude aldehyde intermediate 32) was immediately dissolved in anhydrous dimethylformamide (30 ml) and treated with dimethylformamide dimethylacetal (2.5 ml, 10 mmol). The reaction mixture was stirred at room temperature for 3 hours under anhydrous conditions and then evaporated under vacuum pump pressure (water bath 70°) to yield a dark brown gum. The gum was dissolved in ethyl acetate (50 ml), treated with silica gel (6 g), and the mixture evaporated to dryness in vacuo. The granular material was applied to the top of a shallow bed of silica gel (18 g) in a 60 ml (4.5×2 internal diameter) sintered glass funnel. Elution of this column with solvent A (250 ml) and evaporation of the eluates in vacuo afforded 2.4 g (56%) of the formylated aldehyde 33 as a yellow foam. $R_f$=0.57 (major), 0.65 (minor), solvent A. $^1$H-NMR (CDCl$_3$): δ10.02 (s, 1, CHO); 9.24 (br s, 1, CH=N); 6.24 (d, 1, H(1'), $J_{1',2'}$=2.5 Hz); 3.14, 3.08 (s, s; 3, 3; N,N-dimethyl); 2.08 (m, 9H, COCH$_3$), and a trace of ethyl acetate at 2.0, 1.6 and 4.0. UVλ$_{max}$(nm), (log $_{10}$ ε): methanol, 315 (3.86), 261 (3.92), 224 (4.21); pH 1, 312 (3.79), 263 (3.93); pH 11, 311 (3.81), 264 (3.94), 229 (4.21). This foam contained a small amount of ethyl acetate as a trapped contaminant and this was reflected in its elemental analysis. Anal. Calcd for C$_{17}$H$_{23}$N$_5$O$_8$.0.25CH$_3$CO$_2$C$_2$H$_5$: C, 48.58; H, 5.40; N, 15.58. Found: C, 48.32, H, 5.65; N, 15.65. Evidence for the presence of the minor formylated product in the mixture was seen as a small singlet for its methoxy protons in the $^1$H-NMR at δ4.20.

In preparing 5-(N,N-Dimethylaminomethyleneamino)-4-(cyano[trimethylsiloxy]methyl)-1-(2,3,5-tri-O-acetyl-β-D-ribofuranosyl)-v-triazole, 34, a scrupulously dried 100 ml round bottom flask containing the nucleoside 33 (4.73 g, 6.57 mmol) was sealed with a septum and flushed with nitrogen for 20 min using a dual set of needles. Trimethylsilyl cyanide (TMSCN, 4.3 ml, 34 mmol) was added via a syringe, keeping rigorous anhydrous conditions. The mixture was warmed slightly to effect dissolution and then cooled to 5° in an ice bath. A dilution of BF$_3$.OEt$_2$ in ether (1 ml, 1:10, v/v) was added to the frozen mixture via a syringe and then the mixture was allowed to thaw by a removal of the ice bath. Subsequently, the reaction mixture was allowed warm to room temperature and then stirred under nitrogen for 14 hours. The reaction mixture was cooled to 5° and an additional 1 ml of dilute BF$_3$.OE$_2$ was added. The very dark solution was stirred at room temperature for an additional 6 hours and then evaporated to dryness in vacuo to afford a dark brown residue. The residue was dissolved in solvent system B (8 ml) and this solution was chromatographed on a Michell-Miller column (300 mm length) and precolumn (100 mm length). Both columns had been previously treated with a solution of 2,2-dimethoxypropane in ethyl acetate (200 ml, 3%, v/v) to remove all traces of water. A low pressure chromatography apparatus was used with solvent system B (650 ml) as eluent and maintaining a flow rate of 5 ml/min. The progress of the separation was monitored with an Altex UV detector (254 nm and 200 nm) and TLC (solvent system B) analysis. Three fractions were collected (200 ml/fraction). The second fraction contained the product with $R_f$=0.78. This fraction was evaporated in vacuo to afford 2.83 g (48%) of compound 34 as a light yellow syrup. $^1$H-NMR (CDCl$_3$): δ8.24 (br s, 1, CH=N); 6.30 (m, 1, H(1')); 3.18 (br s, 6, N,N-dimethyl); 2.3–2.1 (m, 9, COCH$_3$). UVλ$_{max}$(nm), (log$_{10}$ ε): methanol, 265 (3.82). Anal. Calcd for C$_{21}$H$_{36}$N$_6$O$_8$Si: C, 48.08; H, 6.14; N, 16.02. Found: C, 48.11; H, 6.03; N, 15.98. The methoxy protons of the minor component of this mixture were just discernible in the $^1$H-NMR Spectrum at δ4.20. The material was judged to contain 2–3% of the minor compound, and this impurity did not significantly alter the elemental analysis as calculated for the major component, compound 34.

To prepare 6,7,8-Trihydro-3-(2,3,5-tri-O-acetyl-β-D-ribofuranosyl)-v-triazolo [4,5-d] [1,3] diazepin-8(R,S)-ol, 36, a 500 ml Parr stainless steel vessel fitted with a scrupulously dried glass sleeve and containing a solution of the nucleoside 34 (0.22 g, 0.42 mmol) in anhydrous p-dioxide (40 ml) was purged with a steady stream of dry nitrogen for 20 min. T-1 Raney nickel (0.30 g weighed wet) was washed with anhydrous p-dioxane (4×10 ml) by decantation. The final suspension was added to the purged solution of the nucleoside 34 and the vessel was sealed. The Parr stainless steel vessel was charged with 450 psi of hydrogen, and then heated to 110° in an oil bath. The equilibrium hydrogen pressure of 510 psi was maintained for 12 hours. After this time, the reduction mixture was filtered through packed Celite (6 g) on a 60 ml (4.5 cm internal diameter) sintered glass funnel and the catalyst and Celite bed was promptly washed with absolute ethanol (50 ml). The combined filtrates were evaporated in vacuo to afford a clear, colorless syrup. This syrup exhibited two major products on TLC corresponding to the trimethylsilyl ether 35 ($R_f$=0.50, solvent system B), and two minor products corresponding to the R and S isomers of 36 ($R_f$=0.10–0.15, solvent system B). The syrup was dissolved in methanol (10 ml), cooled to 0° and treated with cold aqueous acetic acid (2 ml, 20%, v/v). The mixture was stirred at 0° for 3 hours and then the solvents were evaporated in vacuo (water bath, 40°) to yield a thick syrup. The Syrup was dissolved in absolute ethanol (2×20 ml) and toluene (2×20 ml) and each solution was individually evaporated to dryness in vacuo. The resulting residue was triturated with cold ethyl acetate (5 ml) to yield a white precipitate which was collected by filtration. Trituration of this product with a second portion of ethyl acetate (5 ml) yielded 68 mg (39.4%) of 36 as a white powder, mp 162°–165°. $^1$H-NMR (360 MHZ) (DMSO-$d_6$): δ8.28 (m, 1, N-H, exch.); 7.18 (d, 1, H(5), $J_{5,6}$=4 Hz); 6.20 (d, 1, H(1'), $J_{1'2'}$=3.5 Hz); 5.56 (m, 1, -OH, exch.); 4.06 (m, 1, H(8)); 3.21–3.31 (2m, 2, H(7), H(7)); 2.06–1.96 (m, 9, COCH$_3$). UVλ$_{max}$(nm), (log$_{10}$ε): methanol, 279 (4.02); pH 1, 261 (3.91); pH 11, 277 (4.09). Anal. Calcd for C$_{16}$H$_{21}$N$_5$O$_8$: C, 46.72; H, 5.14; N, 17.03. Found: C, 46.45; H, 5.19; N, 16.77.

To synthesize the desired 6,7,8-Trihydro-3-β-D-ribofuranosyl-v-triazole [4,5-d] [1,3] diazepin-8(R,S)-ol, 4 and 37, the mixture of R and S isomers (36, 0.10 g, 0.24 mmol) was dissolved in a saturated solution of ammonia in anhydrous methanol (20 ml, saturated at 0°) in a 200 ml glass pressure bottle. The reaction mixture was stirred at room temperature for 18 hours and then the solvent was evaporated to dryness in vacuo to yield a thick residue. The residue was triturated with chloroform (2×15 ml) and the gum which resulted was placed under vacuum pump pressure for 1 hour. The residue was dissolved in warm ethanol (50°, 3 ml) and then stored at 5° for 18 hours. The crystalline material which had separated from the solution was filtered, washed with cold ethanol (1 ml) and dried in a vacuum oven (50°, 0.1 Torr) for 3 hours to afford 45 mg (64%) of a mixture of 4 and 37 as a white powder, $R_f$=0.29, solvent system E. M.P. 185°–190° (sinters 180°). $^1$H-NMR (360 MHz) (DMSO-$d_6$): δ8.18 (br s, 1, N-H, exch.); 7.13 (d, 1, H(S), $J_{5,6}$=5.0 Hz); 5.94 (d, 1, H(1'), $J_{1',2'}$=5.0 Hz); 4.93 (t, 0.75, C(8)OH, exch., isomer A); 4.87 (t' 0.25, C(8)OH, exch., isomer B); 3.89 (m, 1, H(8)); 3.35–3.15 (m, 2, H(7a),H(7b)). UVλ$_{max}$(nm), (log$_{10}$ ε): methanol, 277 (4.00); pH 1, 260 (3.92); pH 11, 275 (4.08). Anal. Calcd for C$_{10}$H$_{15}$N$_5$O$_5$: C, 42.11; H, 5.30; N, 24.55. Found: C, 42.23; H, 5.47; N, 24.72. For C-13 NMR data, refer to Table III.

HPLC Separation of the mixture of R and S isomers of 6,7,8-Trihydro-3-β-D-ribofuranosyl-v-triazolo [4,5-d] [1,3] diazepin-8-ol, 4 and 37 (0.15 g, 0.53 mmol) was accomplished by first dissolving mixture in water (0.5 ml, deionized through a four-bowl Millipore Milli-Q system, catalog No. ZD2011574). This solution was chromatographed (two injections) on a Whatman Partisil M-20 (10 mm×50 cm) ODS-3 reverse phase silica gel column while maintaining a flow rate of 10 ml/min. A gradient elution of water-methanol (Burdick and Jackson, spectrograde quality) programmedd by a Varian Vista 54 Series liquid chromatograph and Varian CDS 401 data station coupled to a Varian UT 50 variable wavelength detector (at 275 nm) provided a separation of compounds 4 and 37 (see the Figure). Two fractions were collected, centered at times $T_A$=45.5 min. and $T_B$=51.8 min., corresponding to isomers A and B, respectively. These fractions were lyophilized to obtain isomer A (100 mg) as an amorphous glass, and isomer B (33 mg) as a white powder. Isomer A has been tentatively assigned the S configuration of 37 at C(8) and isomer B the R configuration of 4. These assignments have been made based on the relative inhibitory activities against adenosine deaminase of A and B (as previously stated). Isomer A, k' (HPLC)=1.27, $[\alpha]_D^{23}$ −29.4° (c 2.18, H$_2$)). UVλ$_{max}$(nm), (log$_{10}$ ε); methanol, 277 (3.90); pH 1, 260 (3.78); pH 11, 276 (3.96). Isomer B, mp 210° dec., k' (HPCL)-1.59, $[\alpha]_D^{23}$ −79.70 (C 1.33, H$_2$O), UVλ$_{max}$(nm), (log$_{10}$ ε): methanol 279 (3.88); pH 1, 260 (3.88); pH 11, 277 (4.05). For C-NMR data see Table V. For $^1$H-NMR data, See Table V.

TABLE V

H$^1$-NMR (DMSO-$d_6$) (360 MHz) FOR COMPOUNDS 4 AND 37

| Compound/ | Chemical Shifts[a] | |
|---|---|---|
| Proton | 4 | 37 |
| H(5) | 7.13 (d, $J_{5,NH}$ + 3.0 Hz)[b] | 7.13 (d, $J_{5,NH}$ + 3.1 Hz)[b] |
| H(7a,7b) | 3.19 (d), 3.30 (dd, $J_{7a,7b}$ = 12.6 Hz; $J_{7a,8}$ = 4.4 Hz; $J_{7b,8}$ < 1 Hz | 3.19 (d), 3.31 (dd, $J_{7a,7b}$ = 12.8 Hz; $J_{7a,8}$ = 4.4 Hz; $J_{7b,8}$ < 1 Hz |
| H(8) | 3.89 (m, J width ≈ 4.5 Hz) | 3.89 (m, J width ≈ 4.6 Hz) |
| H(1') | 5.93 (d, J1',2' = 4.4 Hz) | 5.94 (d, J1',2' = 4.5 Hz) |
| H(2') | 5.40 (m, J2',3' < 1 Hz) | 5.05 (m, J2',3' < 1 Hz) |
| H(3') | 4.54 (q, J3',4' = 9.6 Hz) | 4.54 (t, J3',4' = 4.7 Hz) |
| H(4') | 4.19 (q, J4',5' = 5.1 Hz) | 4.18 (t, J4',5' = 4.8 Hz) |
| H(5') | 3.55 (m, 3.42 (m, $J_{5a',5b'}$ = 11.9 Hz) | 3.55 (m, 3.40 (m, $J_{5a',5b'}$ = 10.8 Hz) |
| NH | 8.2 (.n)[c] | 8.1 (m)[c] |

[a]Chemical shifts are expressed in ppm downfield from Me$_4$Si. Multiplicities: d, doublet., dd, doublet of doublets; m, multiplit; q, quartet. Concentrations are 3 mg/0.3 ml. Temp. ca. 25° C.
[b]Signal collapses to a singlet upon exchange of N—H with D$_2$O.
[c]Exchanges with D$_2$O.

Having thus described the invention with a certain degree of particularity, it is to be understood that the invention is not limited to the embodiments set forth herein for purposes of exemplification, but is to be limited only by the scope of the attached claims, including a full range of equivalents to which each element thereof is entitled.

I claim:

1. An azolo [1,3] diazepine nucleoside with the structural formula:

2. An azolo [1,3] diazepine nucleoside with the structural formula:
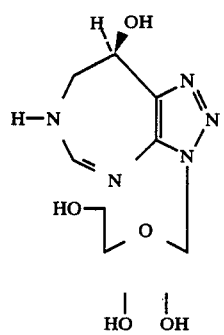
3. An azolo [1,3] diazephine nucleoside R and S isomer mixture with the structural formula:
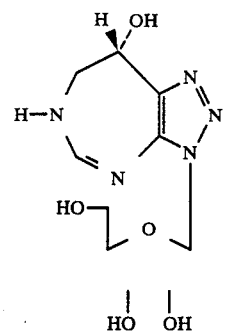
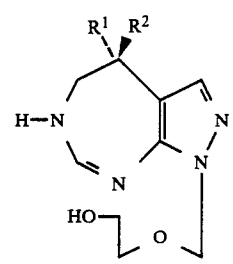
where $R^1$ and $R^2$ are either H or OH and $R^1$ and $R^2$ are not the same.
* * * * *